United States Patent
Siow et al.

(10) Patent No.: US 11,699,231 B2
(45) Date of Patent: Jul. 11, 2023

(54) METHOD FOR ESTABLISHING THREE-DIMENSIONAL MEDICAL IMAGING MODEL

(71) Applicant: CHANG GUNG MEMORIAL HOSPITAL, LINKOU, Taoyuan (TW)

(72) Inventors: Tiing-Yee Siow, Taoyuan (TW); Cheng-Hong Toh, Taoyuan (TW); Cheng-Yu Ma, Taoyuan (TW); Chang-Fu Kuo, Taoyuan (TW)

(73) Assignee: CHANG GUNG MEMORIAL HOSPITAL, LINKOU, Taoyuan (TW)

( * ) Notice: Subject to any disclaimer, the term of this patent is extended or adjusted under 35 U.S.C. 154(b) by 254 days.

(21) Appl. No.: 17/210,604

(22) Filed: Mar. 24, 2021

(65) Prior Publication Data
US 2021/0334958 A1    Oct. 28, 2021

(30) Foreign Application Priority Data
Apr. 28, 2020 (TW) .................................. 109114132

(51) Int. Cl.
*G06T 7/00* (2017.01)
*G06T 3/40* (2006.01)
*G06N 3/084* (2023.01)
*G16H 30/20* (2018.01)

(52) U.S. Cl.
CPC .......... *G06T 7/0012* (2013.01); *G06N 3/084* (2013.01); *G06T 3/4007* (2013.01); *G16H 30/20* (2018.01); *G06T 2207/10016* (2013.01); *G06T 2207/10028* (2013.01); *G06T 2207/10081* (2013.01); *G06T 2207/20081* (2013.01); *G06T 2207/20084* (2013.01); *G06T 2207/30101* (2013.01)

(58) Field of Classification Search
CPC ................. G06T 7/0012; G06T 3/4007; G06T 2207/10016; G06T 2207/10028; G06T 2207/10081; G06T 2207/20081; G06T 2207/20084; G06T 2207/30101; G16H 30/20; G06N 3/084
See application file for complete search history.

(56) References Cited

U.S. PATENT DOCUMENTS

| | | | |
|---|---|---|---|
| 11,354,541 B2* | 6/2022 | Wang | G06T 3/4046 |
| 2019/0289257 A1* | 9/2019 | Schroers | G06N 3/045 |
| 2019/0333623 A1* | 10/2019 | Hibbard | G16H 20/40 |
| 2020/0138522 A1* | 5/2020 | Tikka | A61B 5/4504 |
| 2020/0234471 A1* | 7/2020 | Lu | G06T 7/11 |

\* cited by examiner

*Primary Examiner* — Shefali D Goradia
(74) *Attorney, Agent, or Firm* — Lando & Anastasi, LLP

(57) ABSTRACT

A method for establishing a 3D medical imaging model of a subject is to be implemented by an X-ray computed tomography (CT) scanner and a processor. The method includes: emitting X-rays on the subject sequentially from plural angles with respect to the subject to obtain M number of X-ray images of the subject in sequence; obtaining, for each pair of consecutive X-ray images, K number of intermediate image(s) by using the pair of consecutive X-ray images as inputs to a convolutional neural network (CNN) model that has been trained for frame interpolation; and establishing the 3D medical imaging model by using a 3D reconstruction technique based on the M number of X-ray images and the intermediate images obtained for the M number of X-ray images.

5 Claims, 3 Drawing Sheets

METHOD FOR ESTABLISHING THREE-DIMENSIONAL MEDICAL IMAGING MODEL

CROSS-REFERENCE TO RELATED APPLICATION

This application claims priority of Taiwanese Invention Patent Application No. 109114132, filed on Apr. 28, 2020.

FIELD

The disclosure relates to a method for establishing a three-dimensional medical imaging model, and more particularly to a method for establishing a three-dimensional medical imaging model based on X-ray computed tomography (CT).

BACKGROUND

A conventional three-dimensional reconstruction technique requires a large number of images as inputs for establishing a three-dimensional medical imaging model. In other words, in order to establish a three-dimensional medical imaging model of a subject using the conventional reconstruction technique and X-ray computed tomography (CT), the subject would be exposed to a high dose of X-ray radiation.

SUMMARY

Therefore, an object of the disclosure is to provide a method for establishing a three-dimensional medical imaging model of a subject that can alleviate the drawback of the prior art, and that can reduce the number of images required for establishing the three-dimensional medical imaging model while maintaining the quality of the three-dimensional medical imaging model.

According to the disclosure, the method is to be implemented by an X-ray computed tomography (CT) scanner and a processor. The method includes steps of:
  emitting, by the X-ray CT scanner, X-rays on the subject sequentially from plural angles with respect to the subject so as to obtain M number of X-ray images of the subject in sequence, where M is a positive integer greater than one;
  for each pair of consecutive X-ray images among the M number of X-ray images, obtaining, by the processor, K number of intermediate image(s) by using the pair of consecutive X-ray images as inputs to a convolutional neural network (CNN) model that has been trained for frame interpolation, where K is a positive integer; and
  establishing, by the processor, the three-dimensional medical imaging model of the subject by using a three-dimensional reconstruction technique based on the M number of X-ray images and the intermediate images obtained for the M number of X-ray images, wherein for each pair of consecutive X-ray images, the corresponding K number of intermediate image(s) is (are) to be interpolated between the consecutive input images of the pair.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Figure 1:
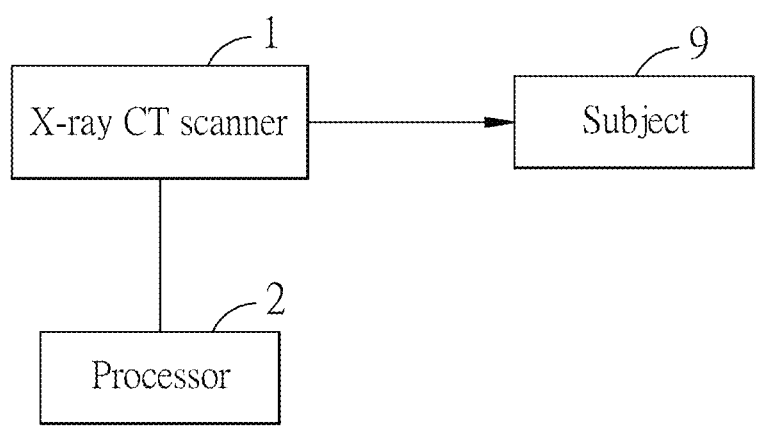
FIG. 1 is a block diagram illustrating an embodiment of a system that includes an X-ray computed tomography (CT) scanner and a processor configured to implement a method for establishing a three-dimensional medical imaging model of a subject according to the disclosure.

FIG. 1 illustrates an embodiment of a system that includes an X-ray computed tomography (CT) scanner 1 and a processor 2 which are utilized to implement a method for establishing a three-dimensional medical imaging model of a subject 9 according to the disclosure.

In this embodiment, the X-ray CT scanner 1 is implemented by a C-Arm X-ray computed tomography (CT) scanner that is capable of capturing plural images of the subject 9 respectively from plural angles with respect to the subject 9.

In this embodiment, the processor 2 may be implemented to be a desktop computer, a laptop computer, a notebook computer, a tablet computer, a central processing unit (CPU), a microprocessor, a micro control unit (MCU), a system on a chip (SoC), or any circuit configurable/programmable in a software manner and/or hardware manner to implement functionalities discussed in this disclosure. However, implementation of the processor 2 is not limited to what are disclosed herein and may vary in other embodiments.

In this embodiment, the subject 9 may be blood vessels in a human body part (e.g., the head), but is not limited thereto.

Figure 2:
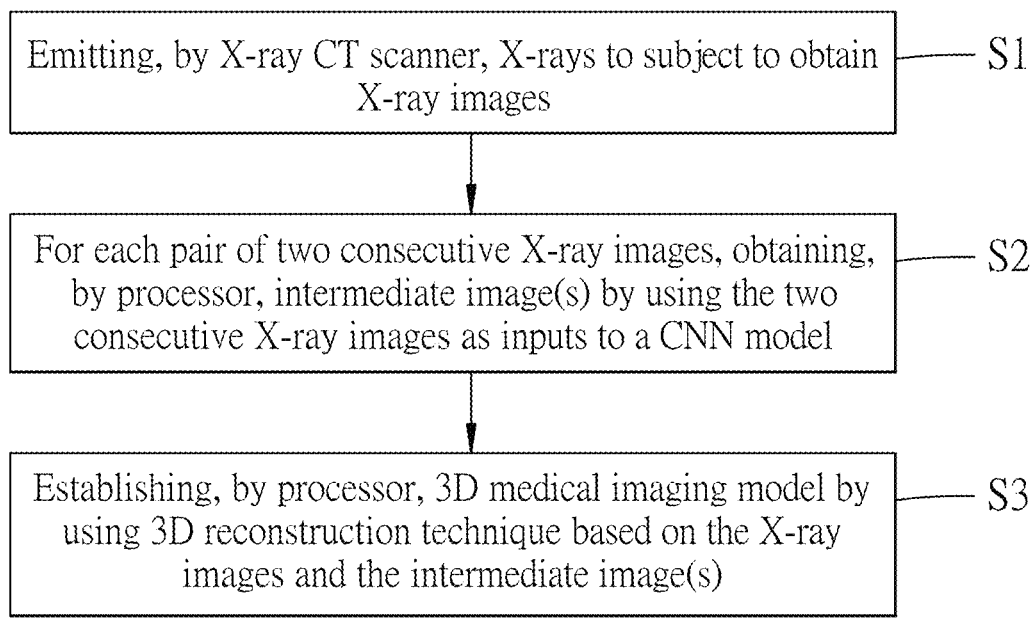
FIG. 2 is a flow chart illustrating an embodiment of the method according to the disclosure.

Referring to FIGS. 1 and 2, the method includes steps S1 to S3 delineated below.

In step S1, the X-ray CT scanner 1 emits X-rays on the subject 9 sequentially from plural angles with respect to the subject 9 so as to obtain M number of X-ray images of the subject 9 in sequence, where M is a positive integer greater than one. The M number of X-ray images respectively correspond to the plural angles from which the X-ray CT scanner 1 emits X-rays on the subject 9. It should be noted that the M number of X-ray images are managed under standards of Digital Imaging and Communications in Medicine (DICOM).

In step S2, for each pair of consecutive X-ray images among the M number of X-ray images, the processor 2 obtains K number of intermediate image(s) by using the pair of consecutive X-ray images as inputs to a convolutional neural network (CNN) model that has been trained for frame interpolation, where K is a positive integer.

In step S3, the processor 2 establishes the three-dimensional medical imaging model of the subject 9 by using a three-dimensional reconstruction technique based on the M number of X-ray images and the intermediate images obtained for the M number of X-ray images, wherein for each pair of consecutive X-ray images, the corresponding K number of intermediate image(s) is/are to be interpolated or inserted between the two consecutive X-ray images of the pair. In this embodiment, the three-dimensional reconstruction technique includes one of the following: the back-projection algorithm, the filtered back-projection algorithm, the Feldkamp-Davis-Kress (FDK) algorithm, the algebraic reconstruction technique, the Fourier transformation, the iterative algorithm, and combinations thereof.

It should be noted that before utilizing the CNN model to obtain K number of intermediate image(s) for each pair of consecutive X-ray images among the M number of X-ray images, the processor 2 trains the CNN model by using N number of X-ray images of a subject that are different from the M number of X-ray images, where N is a positive integer and is equal to M+(M−1)×K. In other embodiments, the CNN model may be trained by a computer or a computing device other than the processor 2.

More specifically, during training of the CNN model, the X-ray CT scanner 1 emits X-rays on a subject, which may be the subject 9 or a different subject, sequentially from plural angles with respect to the subject so as to obtain the N number of X-ray images of the subject in sequence. Thereafter, for every P number (hereinafter also referred to as a window size) of consecutive training images selected from among the N number of X-ray images, where P is a positive integer and is equal to K+2, the processor 2 trains the CNN model by using a first training image and a last training image of the P number of consecutive training images as training inputs to the CNN model, and uses the remaining training image (s) of the P number of consecutive training images as target synthesis image(s) (which serves as ground truth in training the CNN model) for calculating a loss function of the CNN model.

In this embodiment, P (i.e., the window size) ranges from 3 to 12, and K (i.e., the number of intermediate images to be interpolated for each pair of consecutive X-ray images) ranges from 1 to 10.

Figure 3:
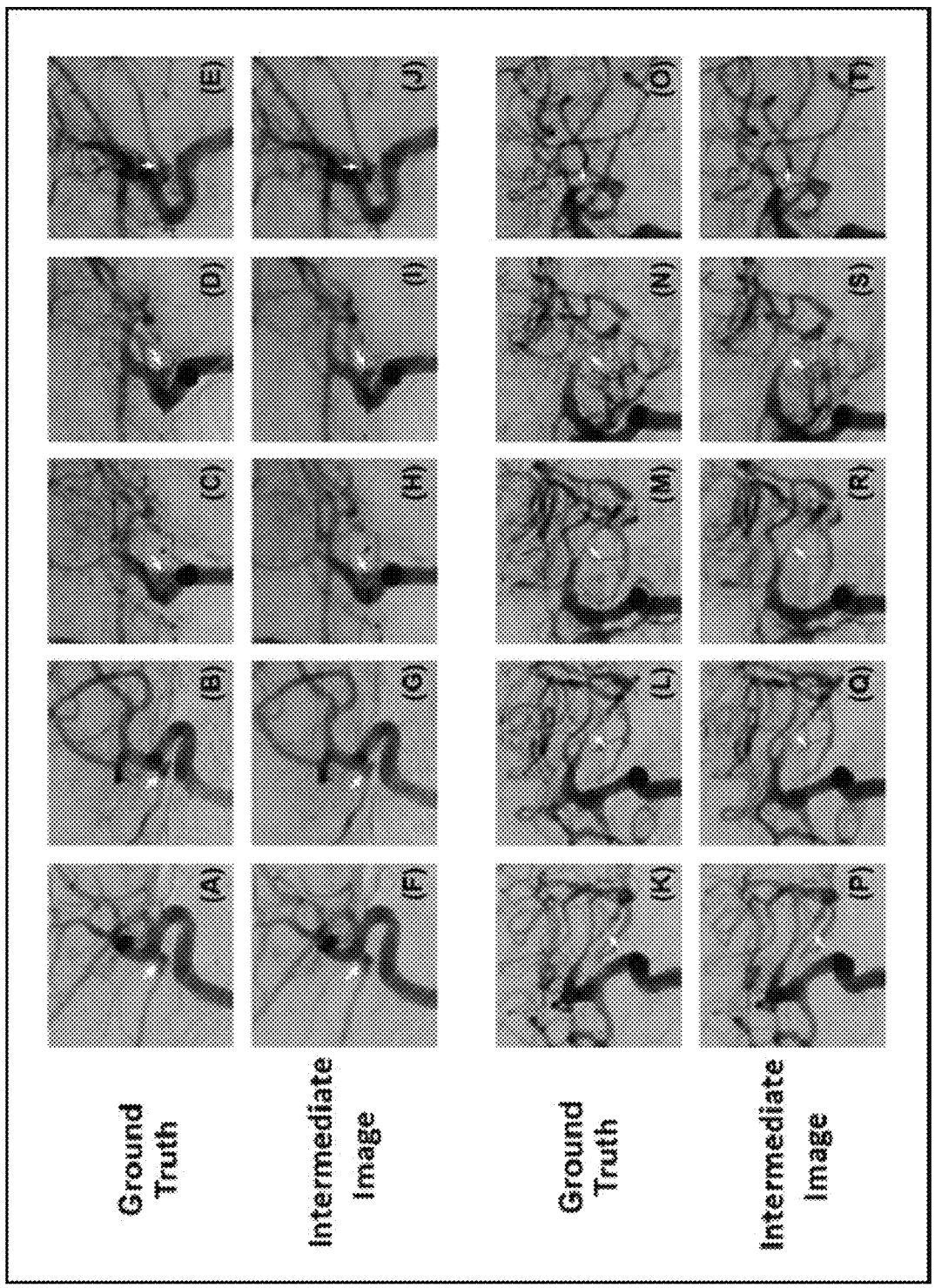
FIG. 3 is a schematic diagram illustrating examples of intermediate images obtained by using the method according to the disclosure.

FIG. 3 illustrates examples of intermediate images obtained from the CNN model according to the disclosure. Parts (A), (B), (C), (D) and (E) of FIG. 3 illustrate images of a carotid artery of a subject who is diagnosed with posterior communicating artery aneurysm (indicated by white arrows), and these images are captured respectively from different projection angles with respect to the subject by using techniques of three-dimensional rotational angiography (3D-RA) and serve as ground truths in training the CNN model. Parts (F), (G), (H), (I) and (J) of FIG. 3 illustrate five intermediate images that respectively correspond to the images in parts (A), (B), (C), (D) and (E) of FIG. 3 and that are obtained from the CNN model according to the disclosure. Evidently, the geometric features of the aneurysm (indicated by white arrows) respectively corresponding to the different projection angles have been successfully reproduced in the five intermediate images in parts (F), (G), (H), (I) and (J) of FIG. 3. Similarly, parts (K), (L), (M), (N) and (O) of FIG. 3 illustrate images of an inferior division of the middle cerebral artery of a subject who is diagnosed with segmental stenosis (indicated by white arrows), and these images are captured respectively from other different projection angles with respect to the subject by using techniques of 3D-RA and serve as other ground truths in training the CNN model. Parts (P), (Q), (R), (S) and (T) of FIG. 3 illustrate five other intermediate images that respectively correspond to the images in parts (K), (L), (M), (N) and (O) of FIG. 3 and that are obtained from the CNN model according to the disclosure. Evidently, the geometric features of the stenotic artery (indicated by white arrows) respectively corresponding to the other different projection angles have been faithfully reproduced in the five other intermediate images in parts (P), (Q), (R), (S) and (T) of FIG. 3.

In this embodiment, the CNN model is implemented to be an optical flow CNN model. Techniques adopted to implement the optical flow CNN model are disclosed in a conference paper entitled "*Super SloMo: High Quality Estimation of Multiple Intermediate Frames for Video Interpolation*," authored by Huaizu Jiang et al. and submitted to Computer Vision and Pattern Recognition (CVPR) 2018.

In brief, the optical flow CNN model includes a first convolutional encoding-decoding module and a second convolutional encoding-decoding module. The first convolutional encoding-decoding module is configured to compute intermediate optical flow based on two input images, where the intermediate optical flow is related to intermediate image (s) to be interpolated between the two input images. The second convolutional encoding-decoding module is configured to synthesize the intermediate image (s) from the two input images and the intermediate optical flow which are used as inputs to the second convolutional encoding-decoding module.

Explanation will now be made as to how the optical flow CNN model is trained with a training sample that includes the training inputs, such as two input images, and the target synthesis image(s) expected to be outputted by the optical flow CNN model. First, the first convolutional encoding-decoding module receives the training inputs, computes, by conducting a deep learning algorithm, the intermediate optical flow for intermediate image(s) to be interpolated between the training inputs, and outputs the intermediate optical flow to the second convolutional encoding-decoding module. Second, the second convolutional encoding-decoding module receives the intermediate optical flow as input, and synthesizes the intermediate image(s) to be interpolated between the training inputs based on the intermediate optical flow and the training inputs. Then, the processor 2 calculates the loss function of the optical flow CNN model based on the target synthesis image(s) and the intermediate image(s) thus synthesized, and adjusts parameter(s) of the optical flow CNN model to minimize the loss function thus calculated.

In an example of training the optical flow CNN model disclosed by Jiang et al., the window size (i.e., P) is nine, and the number of intermediate images to be interpolated for each pair of consecutive X-ray images (i.e., K) is seven. That is to say, for every nine consecutive training images, a first one and a last one of the nine consecutive training images serve as the training inputs to the optical flow CNN model, and the remaining seven consecutive training images serve as the target synthesis images.

In a scenario of this embodiment where M is equal to forty-five and K is equal to two, i.e., there are forty-five X-ray images and two intermediate images are to be interpolated between every pair of consecutive X-ray images, for any pair of consecutive X-ray images (hereinafter also referred to as the $i^{th}$ X-ray image and the $i+1^{th}$ X-ray image, where i is an integer ranging from one to forty-four), the processor 2 obtains two intermediate images (hereinafter referred to as intermediate images "(i)-1-(i+1)" and "(i)-2-(i+1)") by using the $i^{th}$ X-ray image and the $i+1^{th}$ X-ray image as inputs to the CNN model. For example, the processor 2 obtains two intermediate images (i.e., intermediate images "1-1-2" and "1-2-2") by using the $1^{st}$ X-ray image and the $2^{nd}$ X-ray image as inputs to the CNN model, and obtains another two intermediate images (i.e., intermediate images "2-1-3" and "2-2-3") by using the $2^{nd}$ X-ray image and the $3^{rd}$ X-ray image as inputs to the CNN model. Likewise, the processor 2 obtains still another two intermediate images (i.e., intermediate images "44-1-45" and "44-2-45") by using the $44^{th}$ X-ray image and the $45^{th}$ X-ray image as inputs to the CNN model. In this way, eighty-eight intermediate images are obtained in total for the forty-five X-ray images. Finally, the processor 2 establishes the three-dimensional medical imaging model by using the three-dimensional reconstruction technique (e.g., the FDK algorithm) based on the eighty-eight intermediate images and the forty-five X-ray images.

Considering that N=M+(M−1)×K=45+(45−1)×2=133 and P=K+2=2+2=4, 133 additional X-ray images of a subject are required for the training of the CNN model in the scenario mentioned above, and four consecutive training images will be selected from among the 133 additional X-ray images every time, i.e., the window size is four. The 133 additional X-ray images respectively and sequentially correspond to plural angles of emission of X-rays with respect to the subject.

It is worthy to note that the $(3 \times i-2)^{th}$ one of the 133 additional X-ray images for training the CNN model and the $i^{th}$ X-ray image among the forty-five X-ray images for generating the intermediate images correspond to the same angle of emission (of X-rays). For example, the first image of the 133 additional X-ray images and the $1^{st}$ X-ray image among the forty-five X-ray images correspond to the same angle of emission; the fourth image of the 133 additional X-ray images and the $2^{nd}$ X-ray image among the forty-five X-ray images correspond to the same angle of emission; the $133^{rd}$ image of the 133 additional X-ray images and the $45^{th}$ X-ray image among the forty-five X-ray images correspond to the same angle of emission, and so forth.

As previously mentioned, a first one and a last one of the four consecutive training images serve as training inputs to the CNN model, and the remaining two of the four consecutive training images serve as the target synthesis images. For example, among the $35^{th}$ to $38^{th}$ images of the 133 additional X-ray images, the first and last images, specifically, the $35^{th}$ and $38^{th}$ images serve as the training inputs to the CNN model, and the remaining images, namely, the $36^{th}$ and the $37^{th}$ images serve as the target synthesis images.

To sum up, the method according to the disclosure utilizes the CNN model that has been trained for frame interpolation to obtain the intermediate image(s) for each pair of consecutive X-ray images among the total X-ray images of the subject 9, and establishes the three-dimensional medical imaging model by using the three-dimensional reconstruction technique based on the X-ray images and the intermediate images thus obtained. Since a part of the images (i.e., the intermediate images) used to establish the three-dimensional medical imaging model are obtained by means of frame interpolation instead of being actually captured by X-ray CT scanning, the number of X-ray CT scanning iterations may be reduced, and thereby the X-ray radiation dosage to which the subject is exposed may be reduced. Moreover, costs, measured in time and energy expended performing the X-ray CT scanning, may also be reduced.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive directions.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A method for establishing a three-dimensional medical imaging model of a subject, to be implemented by an X-ray computed tomography (CT) scanner and a processor, the method comprising:
    emitting, by the X-ray CT scanner, X-rays on the subject sequentially from plural angles with respect to the subject so as to obtain M number of X-ray images of the subject in sequence, where M is a positive integer greater than one;
    for each pair of consecutive X-ray images among the M number of X-ray images, obtaining, by the processor, at least one intermediate image by using the pair of consecutive X-ray images as inputs to a convolutional neural network (CNN) model that has been trained for frame interpolation; and
    establishing, by the processor, the three-dimensional medical imaging model of the subject by using a three-dimensional reconstruction technique based on the M number of X-ray images and the intermediate images that are obtained for the M number of X-ray images, wherein for each pair of consecutive X-ray images, the corresponding at least one intermediate image is to be interpolated between the consecutive input images of the pair,
    prior to obtaining the at least one intermediate image, the method further comprising:
    training the CNN model by using N number of additional X-ray images, where N is a positive integer and is equal to M+(M−1)×K, where K is a number of the at least one intermediate image for each pair of consecutive X-ray images.

2. The method as claimed in claim 1, prior to training the CNN model, further comprising:
    emitting, by the X-ray CT scanner, X-rays on a subject sequentially from plural angles with respect to the subject so as to obtain the N number of additional X-ray images in sequence; and
    wherein training the CNN model includes:
    for every P number of consecutive training images selected from among the N number of additional X-ray images, where P is a positive integer and is equal to K+2, training, by the processor, the CNN model by using a first image and a last image of the P number of consecutive training images as training inputs of the CNN model, and using at least one remaining image of the P number of consecutive training images as at least one target synthesis image for calculation of a loss function of the CNN model.

3. The method as claimed in claim 1, wherein obtaining at least one intermediate image includes obtaining the at least one intermediate image by using the two consecutive X-ray images as inputs to the CNN model that is an optical flow CNN model.

4. The method as claimed in claim 1, wherein the three-dimensional reconstruction technique includes one of back-projection algorithm, filtered back-projection algorithm, Feldkamp-Davis-Kress (FDK) algorithm, algebraic reconstruction technique, Fourier transformation, iterative algorithm, and combinations thereof.

5. The method as claimed in claim 1, wherein the M number of X-ray images are managed under standards of Digital Imaging and Communications in Medicine (DICOM).

* * * * *